(12) United States Patent
Savage et al.

(10) Patent No.: US 10,231,832 B2
(45) Date of Patent: *Mar. 19, 2019

(54) STENTS FOR PROSTHETIC HEART VALVES

(71) Applicant: Medtronic, Inc., Minneapolis, MN (US)

(72) Inventors: Padraig Savage, Santa Rosa, CA (US); Gianfranco Pellegrini, Santa Rosa, CA (US); Finn Rinne, Santa Rosa, CA (US); Matthew Rust, Windsor, CA (US); Michael Krivoruchko, Forestville, CA (US)

(73) Assignee: Medtronic, Inc., Minneapolis, MN (US)

( * ) Notice: Subject to any disclaimer, the term of this patent is extended or adjusted under 35 U.S.C. 154(b) by 6 days.

This patent is subject to a terminal disclaimer.

(21) Appl. No.: 15/482,032

(22) Filed: Apr. 7, 2017

(65) Prior Publication Data

US 2017/0224478 A1 Aug. 10, 2017

Related U.S. Application Data

(63) Continuation of application No. 14/100,984, filed on Dec. 9, 2013, now Pat. No. 9,649,191, which is a continuation of application No. 13/093,305, filed on Apr. 25, 2011, now Pat. No. 8,623,079.

(60) Provisional application No. 61/327,216, filed on Apr. 23, 2010.

(51) Int. Cl.
*A61F 2/24* (2006.01)

(52) U.S. Cl.
CPC .......... *A61F 2/2418* (2013.01); *A61F 2/2433* (2013.01); *A61F 2/2436* (2013.01); *A61F 2220/0016* (2013.01); *A61F 2230/0017* (2013.01); *A61F 2230/0054* (2013.01); *A61F 2250/0039* (2013.01)

(58) Field of Classification Search
CPC .................................................. A61F 2/2418
See application file for complete search history.

(56) References Cited

U.S. PATENT DOCUMENTS

| 3,671,979 A | 6/1972 | Moulopoulos |
| 4,056,854 A | 11/1977 | Boretos et al. |
| 4,994,077 A | 2/1991 | Dobben |

(Continued)

OTHER PUBLICATIONS

Anderson H R, et al., "Transluminal Implantation of Artifical Heart Valves" EUR Heart J., 1992; 13:704-708.

(Continued)

*Primary Examiner* — Suba Ganesan
(74) *Attorney, Agent, or Firm* — Medler Ferro Woodhouse & Mills PLLC

(57) ABSTRACT

A stented valve including a stent structure having a generally tubular body portion, an interior area, a longitudinal axis, an first end, an second end, and an outer surface; at least one outflow barb extending from the outer surface of the stent adjacent to the first end of the stent structure and toward the second end of the stent structure; at least one inflow barb extending from the outer surface of the stent adjacent to the second end of the stent structure and toward the first end of the stent structure; and a valve structure attached within the interior area of the stent structure.

18 Claims, 5 Drawing Sheets

(56) References Cited

U.S. PATENT DOCUMENTS

| | | | |
|---|---|---|---|
| 5,332,402 | A | 7/1994 | Teitelbaum |
| 5,370,685 | A | 12/1994 | Stevens |
| 5,397,351 | A | 3/1995 | Pavcnik et al. |
| 5,554,185 | A | 9/1996 | Block et al. |
| 5,855,601 | A | 1/1999 | Bessler et al. |
| 6,168,614 | B1 | 1/2001 | Anderson et al. |
| 7,018,406 | B2 | 3/2006 | Seguin et al. |
| 7,462,191 | B2 | 12/2008 | Spenser et al. |
| 2002/0032481 | A1 | 3/2002 | Gabbay |
| 2003/0199963 | A1 | 10/2003 | Tower et al. |
| 2003/0199971 | A1 | 10/2003 | Tower et al. |
| 2004/0034411 | A1 | 2/2004 | Quijano et al. |
| 2005/0137690 | A1* | 6/2005 | Salahieh ............... A61F 2/2418 623/2.11 |
| 2005/0222674 | A1 | 10/2005 | Paine |
| 2006/0149360 | A1 | 7/2006 | Schwammenthal et al. |
| 2008/0140189 | A1 | 6/2008 | Nguyen et al. |
| 2008/0172119 | A1 | 7/2008 | Yamasaki et al. |
| 2009/0216312 | A1 | 8/2009 | Straubinger et al. |
| 2009/0216314 | A1* | 8/2009 | Quadri ............... A61F 2/2418 623/1.17 |
| 2009/0287299 | A1 | 11/2009 | Tabor et al. |
| 2010/0094411 | A1 | 4/2010 | Tuval et al. |
| 2010/0298931 | A1* | 11/2010 | Quadri ............... A61F 2/2418 623/2.11 |
| 2011/0098800 | A1* | 4/2011 | Braido ............... A61F 2/2412 623/1.16 |

OTHER PUBLICATIONS

Anderson J.R., et al., "Transluminal Catheter Implantation of New Expandable Artifical Cardiac Valve" EUR Heart J.,1990, 11: (Suppl) 224a.

Block P C, "Clinical and Hermodynamic Follow-up After Percutaneous Aortic Valvuloplasty in the Eldery", the American Journal of Cardiology, vol. 62, Oct. 1, 1009.

Bonhoeffer, P. et al. "Percutaneous Insertion of the Pulmonary Valve", J Am Coll Cardiol, 2002; 39: 1664-1669.

Bonhoeffer, P. et al. "Transcatheter Implantation of a Bovine Valve in Pulmonary Position", Circulation, 2002; 102: 813-816.

Boudjemline, Y., "Percutaneous Implantation of a valve in the Descending Aorta in Lambs" EUR Heart J. 2002; 23: 1045-1049.

Boudjemline, Y., "Steps Toward Percutaneous Aortic Valve Replacement", Circulation, 2002; 105: 775-558.

Cribier A. et al., "Percutaneous Transcatheter Implantation of an Aortic Valve Prosthesis for Calcific Aortic Stenosis", Circulation, 2002; 106: 3006-3008.

Hilbert S.L., Evaluation of Explanted Polyurethane Trileaflet Cardiac Valve Prosthesis, J. Thorac Cardiovascular Surgery, 1989; 94: 419-29.

Kulkinski, D., "Future Horizons in Surgical Aortic Valve Replacement: Lessons Learned During the Early Stages of Developing a Transluminal Implantation Technique", ASAIO J, 2004; 50: 364-68.

* cited by examiner

STENTS FOR PROSTHETIC HEART VALVES

RELATED APPLICATIONS

This application is a Continuation of U.S. patent application Ser. No. 14/100,984, filed Dec. 9, 2013, which is a Continuation of U.S. patent application Ser. No. 13/093,305, filed Apr. 25, 2011, now U.S. Pat. No. 8,623,079, which claims the benefit of U.S. Provisional Patent Application Ser. No. 61/327,216, filed Apr. 23, 2010, the entire disclosures of which are incorporated herein by reference.

TECHNICAL FIELD

The present invention relates to prosthetic heart valves. More particularly, it relates to devices, methods, and delivery systems for percutaneously implanting prosthetic heart valves.

BACKGROUND

Diseased or otherwise deficient heart values can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a small opening in the skin of the patient into which a valve assembly is inserted in the body and delivered to the heart via a delivery device similar to a catheter. This technique is often preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stem, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39:1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible.

Other percutaneously delivered prosthetic heart valves have been suggested having a generally similar configuration, such as by Benhoeffer, P. et al., "Transcatheter Implantation of a Bovine Valve in Pulmonary Position." Circulation, 2002; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons that are sometimes used to expand the stent. Thus, with these transcatheter techniques, conventional sewing of the prosthetic heart valve to the patient's native tissue is not necessary. Similarly, in an article by Bonhoeffer, P. et al. titled "Percutaneous Insertion of the Pulmonary Valve," J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Although there have been advances in percutaneous valve replacement techniques and devices, there is a continued desire to provide different designs of cardiac valves that can be implanted in a minimally invasive and percutaneous manner.

SUMMARY

The replacement heart valves of the invention each include a stent having an interior area to which a valve structure is attached. These stents can include a wide variety of structures and features that can be used alone or in combination with features of other stents of the invention. Many of the structures are compressible to a relatively small diameter for percutaneous delivery to the heart of the patient, and then are expandable either via removal of external compressive forces (e.g., self-expanding stents), or through application of an outward radial force (e.g., balloon expandable stents). The devices delivered by the delivery systems described herein can be used to deliver stents, valved stents, or other interventional devices such as ASD (atrial septal defect) closure devices, VSD (ventricular septal defect) closure devices, or PFO (patent foramen ovale) occluders.

Methods for insertion of the replacement heart valves of the invention include delivery systems that can maintain the stent structures in their compressed state during their insertion and allow or cause the stent structures to expand once they are in their desired location. The methods of implanting valves of the invention may include implantation of the stent structures using either an antegrade or retrograde approach. Further, in many of the delivery approaches of the invention, the stent structure is rotatable in vivo to allow the stent structure to be positioned in a desired orientation.

The stent structures of the invention include a series of diamond-shaped structures arranged in adjacent rows along the length of the stent. The stents are generally flared outwardly at their outflow end as compared to their inflow end when the stent is in its deployed location within a patient. Each stent can include attachment features (e.g., loops or apertures) at one end (e.g., its outflow end) for engagement with a feature of a delivery system, and can include fewer crowns at the outflow end than at the inflow end. The stent can alternatively or additionally include attachment features at its inflow end, such as can be useful for stents that are delivered in a transapical manner. The stents can further include a concave annular saddle region that will help in sealing the stent against the annulus and native leaflets and help to minimize paravalvular leakage. The stents can also be provided with outflow and inflow barbs that are located generally in the area of the annular saddle region. The barbs can be positioned to extend toward each other from opposite ends of the stent to prevent or minimize stent migration in both the retrograde and antegrade directions when the stent is implanted in a patient. At least some of the barbs are positioned so that their distal ends are generally within the annular saddle region.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
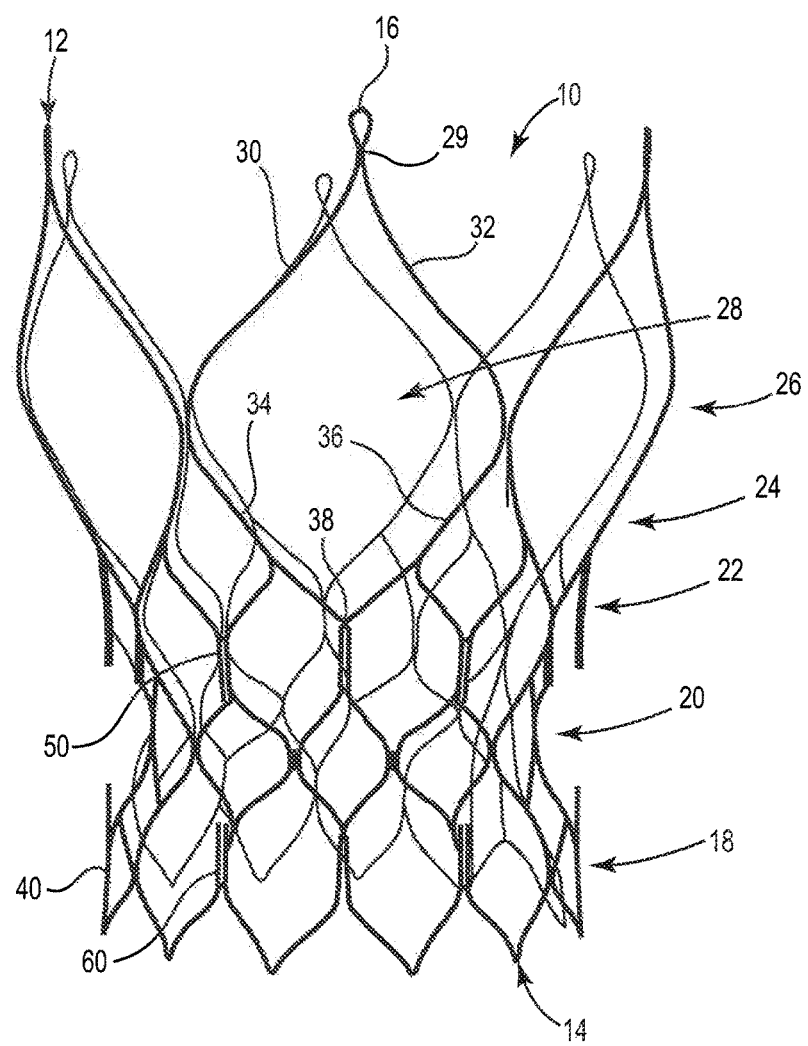
FIGS. 1-3 are front views of one exemplary embodiment of a stent structure, in accordance with the invention.
Figure 2:
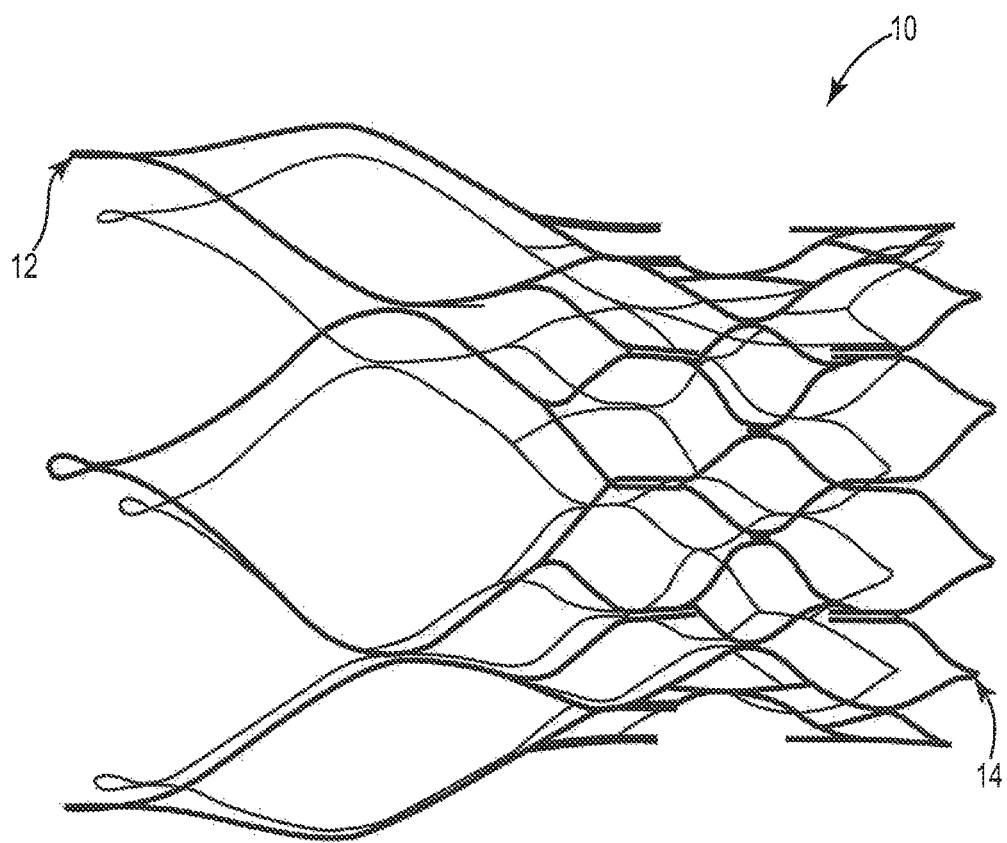
Figure 3:
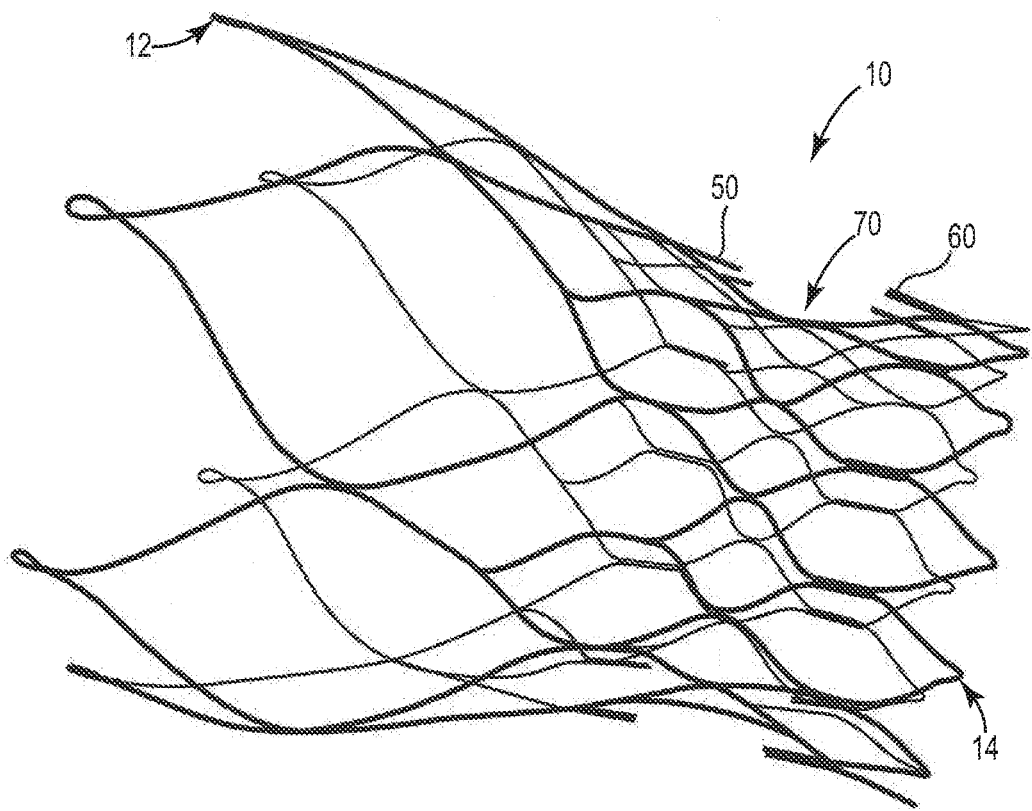
Figure 4:
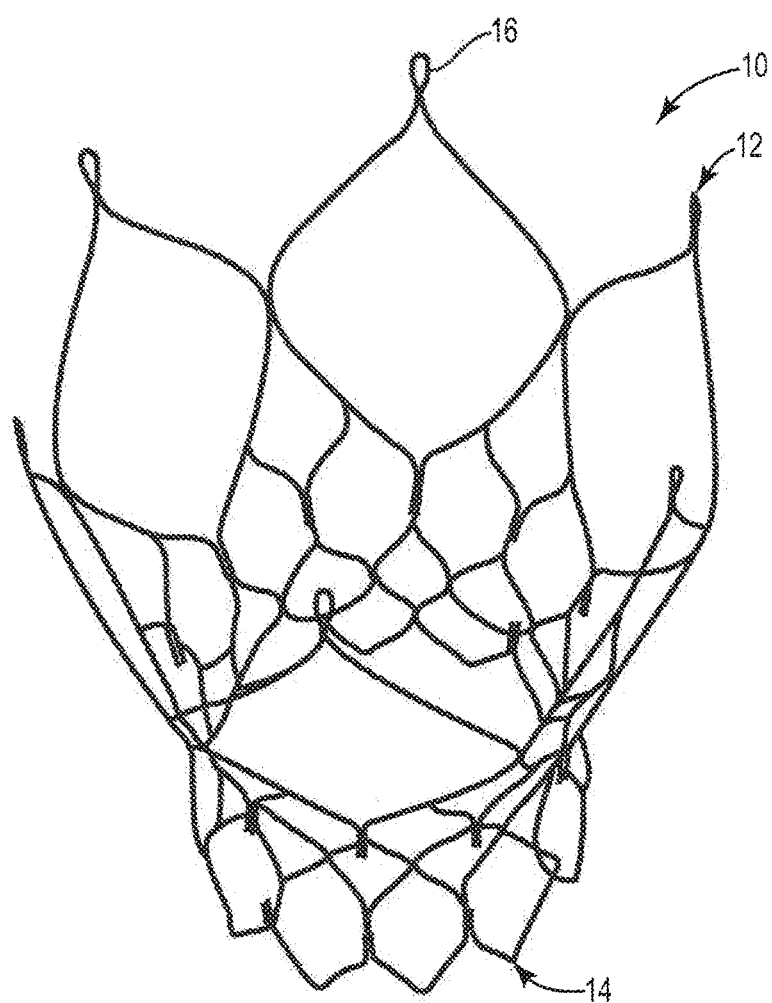
FIG. 4 is a top perspective view of the stent structure of FIGS. 1-3.

As referred to herein, the prosthetic heart valves used in accordance with various devices and methods of heart valve delivery may include a wide variety of different configurations, such as a prosthetic heart valve having tissue leaflets or a synthetic heart valve having polymeric, metallic, or tissue-engineered leaflets, and can be specifically configured for replacing any heart valve. That is, while much of the description herein refers to replacement of aortic valves, the prosthetic heart valves of the invention can also be used in other areas of the body, such as for replacement of native mitral, pulmonic, or tricuspid valves, for use as a venous valve, or to replace a failed bioprosthesis, such as in the area of an aortic valve or mitral valve, for example.

Although each of the stents or frames described herein typically includes leaflets attached within their internal areas, the leaflets are not shown in the illustrated embodiments in order to more clearly see the various described stent features. In general, the stents described herein include a support structure comprising a number of strut or wire portions arranged relative to each other to provide a desired compressibility, strength, and leaflet attachment zone(s) to the heart valve. Other details on particular configurations of the stents of the invention are also described below; however, in general terms, stents of the invention are generally tubular support structures, having leaflets secured within each support structure to provide a valved stent. The leaflets can be formed from a variety of materials, such as autologous tissue, xenograph material, or synthetics, as are known in the art. The leaflets may be provided as a homogenous, biological valve structure, such as a porcine, bovine, or equine valve. Alternatively, the leaflets can be provided as independent structures (e.g., as can be formed with bovine or equine pericardial leaflets) and subsequently assembled to the support structure of the stent. In another alternative, the stent and leaflets can be fabricated at the same time, such as may be accomplished using high strength nano-manufactured NiTi films of the type produced at Advanced Bio Prosthetic Surfaces Ltd. (ABPS) of San Antonio, Tex., for example. The support structures are generally configured to accommodate three leaflets; however, the replacement prosthetic heart valves of the invention can incorporate more or less than three leaflets.

In more general terms, the combination of a support structure with one or more leaflets can assume a variety of other configurations that differ from those shown and described, including any known prosthetic heart valve design. In certain embodiments of the invention, the support structure with leaflets utilize certain features of known expandable prosthetic heart valve configurations, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodyamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105:775-558; Bonhoeffer, P., "Transcatheter Implantation of a Bovine Valve in Pulmonary Position, a Lamb Study", Circulation, 2000; 102:813-816; Boudejmline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Orientation and positioning of the stents of the invention may be accomplished either by self-orientation of the stents (such as by interference between features of the stent and a previously implanted stent or valve structure) or by manual orientation of the stent to align its features with anatomical or previous bioprosthetic features, such as can be accomplished using fluoroscopic visualization techniques, for example. In some embodiments, when aligning the stents of the invention with native anatomical structures, they should be aligned so as to not block the coronary arteries, and native mitral or tricuspid valves should be aligned relative to the anterior leaflet and/or the trigones/commissures.

The various stents or support structures described herein can be a series of wires or wire segments arranged so that they are capable of transitioning at least once, and preferably multiple times, from a collapsed state to an expanded state. A number of individual wires comprising the support structure can be formed of a metal or other material. These wires are arranged in such a way that a support structure can be folded or compressed to a contracted state is which its internal diameter is at least somewhat reduced from its internal diameter in an expanded state. In its collapsed state, such a support structure with attached valves can be mounted on a delivery device. The support structure is configured so that it can be changed to its expanded state when desired, such as by the expansion of a balloon catheter or by the removal of external forces. The delivery systems used for such a stent should be provided with degrees of rotational and axial orientation capabilities in order to properly position the new stent at its desired location.

The wires of the support structure of the stents in other embodiments can be formed from a shape memory material such as a nickel titanium alloy (e.g., Nitinol) or a very high-tensile material that will expand from its compressed state to its original state after removal of external forces. With this material, the support structure is self-expandable from a contracted state to an expanded state, such as by the application of heat, energy, and the like, or by the removal of external forces (e.g., compressive forces). This support structure can be repeatedly compressed and re-expanded without damaging the structure of the stent. In addition, the support structure of such an embodiment may be laser cut from a single piece of material or may be assembled from a number of different components. For these types of stent structures, one example of a delivery system that can be used includes a catheter with a retractable sheath that covers the stent until it is to be deployed, at which point the sheath can be retracted to allow the stent to expand. Alternatively, the stent structures of the invention can be implanted using conventional surgical techniques and/or minimally invasive surgical procedures. In such cases, the stents of the invention can advantageously require relatively few or no sutures to secure the stent to an anatomical location within the patient.

Referring now to the Figures, wherein the components are labeled with like numerals throughout the several Figures and initially to FIGS. 1-4, a stent or stent frame 10 is illustrated. Stent 10 includes a first end 12 having six peaks or crowns and a second end 14 having twelve peaks or crowns. In this embodiment, the first end 12 may be considered to be the outflow end of the stent and the second end 14 may be considered to be the inflow end of the stent, which refers to the direction of blood flow relative to the stent once it is implanted in a patient. It is understood, however, that the first end 12 may instead be the inflow end of the stent and that the second end 14 may instead be the outflow end of the stent.

At least one of the stent crowns of stent 10 at the first end 12 includes a loop or aperture 16, which can be used for attachment to a delivery system, for example. It is contemplated that each of the crowns at the first end 12 includes such a loop or aperture 16 or that only some of the crown include such loops. The size and shape of the loops 16 can all be the same on a single stent, or they can have different sizes and/or shapes. In any case, the loops 16 can be selected or designed for engagement with one or more features of a delivery system that will be used to place the stent in a desired location within a patient, and can specifically be configured to allow for removable attachment of the stent relative to the delivery system. The stents 10 may alternatively or additionally include more or less crowns at either or both ends, and can alternatively or additionally include connectors, such as loops or apertures, at the end 14.

Stent 10 generally includes a series of modified diamond-shaped structures arranged in adjacent rows, where each of the diamond structures or shapes is defined by a series of wires or wire segments. Due to the diamond shape of these structures, at least one "peak" of each diamond-shaped structure of one row coincides with a "valley" created by two circumferentially adjacent diamond-shaped structures in an adjacent row. That is, a single row of diamond-shaped structures can be defined by multiple diamond-shaped structures that are circumferentially adjacent to each other around the stent and that are spaced at a similar longitudinal distance relative to the stent ends. Further, the phrase "adjacent row" used herein refers to a row of diamond structures that is located closest to, or interconnecting with, another row of diamond structures along the longitudinal direction of the stent.

The references herein to "diamond" shaped structures are intended to refer generally to the four-sided shapes illustrated, which can include straight, curved, and/or a combination of straight and curved wire segments. The diamond shape structures further include intersection points or base areas where two adjacent wires or wire segments meet. It is understood that these intersection points or base areas can be generally curved or include a radius, as shown, or that the intersection points can include sharper angles between wire segments. As shown in FIG. 1, each diamond structure includes two intersection points that are spaced from each other along the length of the stent 10, which can be referred to as "peaks" of one row, or can alternatively be referred to as the "valleys" of an adjacent row. The diamond structures further include two intersection points that are spaced from each other relative to the circumference of the stent 10. It is noted also this description is meant to be general relative to the diamond shape of the structures in that it is contemplated that each of the structures can include wires that are curved or otherwise contoured such that sharp intersection points are not created between wires or wire segments. In such cases, a change of curvature of a wire segment can be considered to be a defining point or junction between sides of a diamond-shaped structure. It is further noted that the entire stent may be made of a single piece of material, such that references made herein to wires or wire segments is intended to encompass certain portions of the shapes rather than actual separate pieces of wire that are attached to each other. In other embodiments, multiple wire segments can be arranged and attached to provide the desired stent structure.

With particular reference again to FIGS. 1-4, stent 10 includes a series of adjacent rows of diamond-shaped structures. In particular, stent 10 includes a first row 18 of such structures at second end 14 of the stent, wherein this particular embodiment includes twelve of the diamond-shaped structures in row 18. A row 20 of diamond-shaped structures is adjacent to row 18 and also includes twelve diamond-shaped structures, wherein each of the structures of row 20 shares at least a portion of two wire segments with structures of row 18. The next row 22 is adjacent to row 20 and again includes twelve diamond-shaped structures, wherein each of the structures of row 22 shares at least a portion of two wire segments with structures of row 20. The next row 24 includes six diamond-shaped structures, which are spaced from each other around the circumference of stent 10 in such a way that they do not touch each other. Each of these structures of row 24 shares two wire segments with the structures of adjacent row 22. The next row 26 is adjacent to row 24 and is located at the first end 12 of the stent. This row 26 includes six diamond-shaped structures that are shown in this embodiment as having a relatively large central opening as compared to the other diamond-shaped structures of the stent. In this row 26, the diamond-shaped structures are not spaced from each other like the structures of row 24, but instead extend from each other around the circumference of the stent.

In order to better describe the configuration of one of the diamond-shaped structures of row 26, one exemplary diamond-shaped structure 28 will be described in detail. In particular, structure 28 includes a crown 29 located at the first end 12 of the stent. One of the loops 16 is shown as extending from this crown 29. Two arms 30, 32 extend away from each other at an angle from this crown 29 and toward the second end 14 of the stent. The end of each of these arms 30, 32 that is spaced from the crown 29 terminates at a point or area of intersection with an adjacent diamond-shaped structure of row 26. Structure 28 further includes two additional arms 34, 36 that extend from the ends of arms 30, 32, respectively, and which meet each other at an intersection point or junction 38. It is noted that the junction 38 is spaced longitudinally from the crown 29 along the length of the stent 10 and that the junction 38 can also be considered to be the lowest point of the "valley" between two "peaks" of adjacent structures of row 22. It is further noted that each of the arms 34, 36 includes a first segment that is a shared wire segment with one of the diamond-shaped structures of row 24 and a second segment that is a shared wire segment with one of the diamond-shaped structures of row 22. In this way, the stent 10 includes a reduced number of crowns at the first end 12 as compared to the second end 14, while providing a configuration where the row 26 at the first end 12 includes structures that are immediately adjacent to one another around the circumference of the stent (i.e., the structures of row 26 are not spaced from each other, as are the structures of row 24).

With this reduction in the number of structures at the first end 12 of the stent (and corresponding crowns or peaks of these structures) as compared to the number of structures at the second end 14 of the stent, for example, the open cell area is increased when the device is placed in the intended anatomical position within a patient. This can provide the following advantages: increased percutaneous coronary intervention (PCI) access; increased perfusion to the coronaries, which can improve blood flow; a greater crimped cell area to prevent or minimize pinching of tissue between struts; and a reduction in the accumulated volume (i.e., less stent material) for the crimping operation, thereby providing increased packing efficiency.

Stent 10 further includes a barb 50 extending from at least one of the junctions 38 (i.e., base of the structure or structures 28). In this embodiment, these barbs 50 may also be referred to as "outflow barbs"; as they are located nearest the end of the stent 10 that can be used as the outflow end. In other embodiments, the barbs can be differently placed such that they may instead be closer to the end of the stout that is used in the inflow end. In any case, as shown in this embodiment, one barb 50 extends from each of the junctions 38 toward the second end 14 of the stent, although it is understood that all of the junctions 38 may not have such an extending barb 50. The barbs 50 are configured to be at an angle relative to the other wires of the stent 10 so that they extend at least slightly outward relative to the outer surface of the stent structure. In other words, the barbs 50 of this embodiment do not closely follow the outer shape of the stent, but are intended to protrude or extend at least slightly from this outer stent shape so that there is a space between the outer surface of the stent and the barb 50. In this embodiment, due to the inward curve of the stent 10 in the area of row 20, the barbs 50 extend in a generally parallel direction relative to a longitudinal axis of the stent 10, which results in the barbs extending at least slightly outward relative to the stent structure. However, the barbs 50 may be angled differently relative to the longitudinal axis of the stent 10. In any case, one or more of the barbs 50 can have a free end that is sharp enough to engage with tissue for implantation of the stent, as is described in further detail below. Alternatively, one or more of the barbs 50 can include a more blunt end, which can be used more as a "stop" to minimize migration of the stent when it is positioned within the patient.

Stent 10 further includes at least one barb 60 extending from a junction 40 between arms at the second end 14 of the stent. These barbs 60 may also be referred to as "inflow barbs", as they are located nearest the end of the stent 10 that can be used as the inflow end. In other embodiments, the barbs can be differently placed such that they may instead be closer to the end of the stent that is used as the outflow end. In any case, as shown in this embodiment, one barb 60 extends from each of the junctions 40 toward the first end 12 of the stent, although it is understood that all of the junctions 40 may not have such an extending barb 60. The barbs 60 are configured to be at an angle relative to the other wires of the stent 10 so that they extend at least slightly outward from the outer shape of the stent structure. As with the barbs 50, the barbs 60 of this embodiment do not closely follow the outer shape of the stent, but are intended to protrude or extend at least slightly from this outer stent shape so that there is a space between the outer surface of the stent and the barb 60. In this embodiment, due to the inward curve of the stent 10 in the area of row 20, the barbs 60 also extend in a generally parallel direction relative to a longitudinal axis of the stent 10 and are therefore extending at least slightly outward relative to the stent structure. However, the barbs 60 may be angled differently relative to the outer surface of the stent 10. In any case, one or more of the barbs 60 can have a free end that is sharp enough to engage with tissue for implantation of the stent 10, as is discussed in further detail below. Alternatively, one or more of the barbs 60 can include a more blunt end.

Thus, this embodiment of stent 10 includes two sets of barbs 50, 60, which extend from areas that are at generally opposite ends of the stent and extend toward each other. In the embodiment of FIGS. 1-4, stent 10 comprises a single piece construction, including the barbs 50, 60, which can be provided via a number of manufacturing methods, such as by stamping, laser cutting, and the like. It is also contemplated, however, that the wire structure instead consists of multiple wire segments attached to each other in various locations to make up this structure and/or that the barbs 50, 60 are separate pieces that are welded or otherwise bonded to the stent structure. Each of the barbs 50, 60 are preferably configured in such a way that they do not interfere with the operation of crimping the stent and so that they do not add substantial bulk to the crimped stent.

In FIGS. 1-4, stent 10 is illustrated in its expanded or partially expanded condition. This illustrated condition is intended to represent the general stent condition as it can be configured when it is implanted within the anatomy of a patient. In this expanded condition, stent 10 is generally configured to have a relatively small diameter at the second end 14 as compared to the diameter of its first end 12. That is, the first end 12 is flared at least slightly outwardly relative to the second end 14. The outward flare at the end 12 of the stent 10 (i.e., away from the central longitudinal axis of the stent) can prevent or minimize leakage between the implanted heart valve and the native annulus and/or to provide a physical and/or visual docking feature to secure the stent against a wall of a vessel or opening in the heart to prevent migration of the stent, for example.

Stent 10 further includes an integrated saddle area 70 (see FIG. 3), which is generally located in the area between the inflow and outflow barbs 50, 60 in the area of row 20, and which includes a concave shape relative to the outer surface of the stent 10 adjacent to the end 14. This saddle area 70 may be more or less pronounced than shown, and can be designed in such a way that the shape of the saddle area 70 will help to seal the stent against the annulus and native leaflets in the implantation area of the patient. However, the saddle should not be so pronounced that it would "pinch" the annulus and negatively affect the sealing of the valve against the anatomy. In addition, the saddle area 70 can help to properly position the stent 10 in the patient, either by using visual or tactile feedback. This saddle area 70 can have a relatively high radial force, which aids in active fixation and which helps to prevent or minimize paravalvular leakage.

Figure 5:
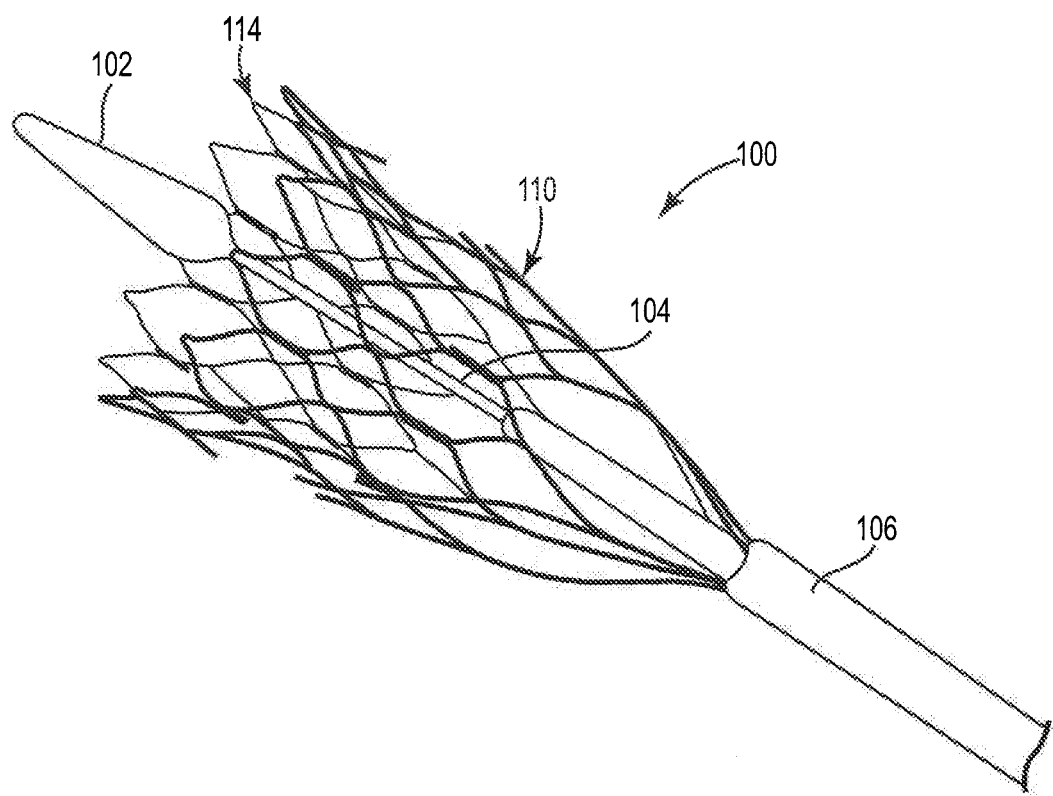
FIG. 5 is a front view of the stent structure of FIG. 1-4 as it has been partially deployed by an exemplary delivery system.

FIG. 5 illustrates a portion of an exemplary delivery system 100, onto which a stent 110 is loaded. Delivery system 100 includes a distal end or tip 102 from which a central longitudinal shaft 104 extends in a proximal direction along the length of the delivery system. Stent 110 includes a first end that is not visible, as it is enclosed within a sheath of the delivery system, and a second end 114. Stent 110 is generally configured as a series of wires or wire segments that can have the same or a similar structure to that of stent 10 illustrated in FIGS. 1-4. As with other stent embodiments described herein, this stent 110 is shown without an internal valve in order to better illustrate the structure of the stent. However, in order to replace a valve (e.g., a heart valve) within a patient, a valve structure would be attached within the internal area of the stent 110 prior to implantation of the stent.

Stent 110 is illustrated with its first end (not visible) being held in a compressed or crimped condition within a sheath 106 of the delivery system 100, and with the remainder of the stent 110 being expanded or partially expanded relative to the sheath 106. The partially expanded condition of the device can be used to assess valve location, paravalvular leakage and valve function. As is described in further detail below, the stent may be delivered to its desired location within the patient using a delivery system of this type with the stent contained within the sheath, and then the sheath can be completely retracted from the stent 110, thereby allowing it to expand to its fully deployed, condition. It is understood that this type of delivery system is appropriate for use when the stent 110 is made of a shape memory material; however, stent 110 may instead be made of a material that is not self-expanding such that the delivery system would then include an expandable balloon that causes the expansion of the stent to its deployed condition.

Delivering the stents of the invention to the implantation location can be performed percutaneously. In general terms, this includes providing a transcatheter assembly, including a delivery catheter, a balloon catheter (in some cases), and a guide wire. In cases that utilize a balloon catheter, such a catheter can define a lumen within which the guide wire is slideably disposed. Further, such a balloon catheter would include a balloon that is connected to an inflation source. It is noted that if the stent being implanted is a self-expanding type of stent, the balloon would not be needed and a sheath or other restraining means would be used for maintaining the stent in its compressed state until deployment of the stent, as described herein. In either case, the transcatheter assembly is appropriately sized for a desired percutaneous approach to the implantation location. For example, the transcatheter assembly can be sized for delivery to the heart valve via an opening at a carotid artery, a jugular vein, a sub-clavian vein, femoral artery or vein, or the like. Essentially, any percutaneous intercostals penetration can be made to facilitate use of the transcatheter assembly. Alternatively, the system can be delivered using a transapical approach.

Prior to delivery, the stent is mounted on the delivery system and compressed to be as small as possible without causing permanent deformation of the stent structure. A sheath may then be slid over the stent to provide a smoother surface for delivery of the stent and/or to maintain the stent in its compressed condition until its deployment. With the stent mounted to the delivery system, the transcatheter assembly is delivered through a percutaneous opening in the patient via the delivery catheter. The implantation location can optionally be located by inserting a guide wire into the patient, which guide wire extends from a distal end of the delivery catheter, and then advancing the delivery catheter along the guide wire. In an alternative embodiment, the stent is delivered to an implantation location via a minimally invasive surgical incision (i.e., non-percutaneously). In another alternative embodiment, the stent is delivered via open heart/chest surgery. In one embodiment of the stents of the invention, the stent includes a radiopaque, echogenic, or MRI visible material to facilitate visual confirmation of proper placement of the stent. The techniques described relative to placement of the stent within the heart can be used both to monitor and correct the placement of the stent in a longitudinal direction relative to the length of the anatomical structure in which it is positioned.

Once the stent is properly positioned, the sheath can be moved in a proximal direction to expose the stent. If a balloon-expandable stent is being deployed, the balloon catheter can then be activated to inflate the balloon, thus transitioning the stent to an expanded state. If a self-expanding stent is being deployed, this removal of the sheath can allow the stent to expand to its expanded state.

One or more markers on the valve, along with a corresponding imaging system (e.g., echo, MRI, etc.) can be used with the various repositionable delivery systems described herein in order to verify the proper placement of the valve prior to releasing it from the delivery system. A number of factors can be considered, alone or in combination, to verify that the valve is properly placed in an implantation site, where some exemplary factors are as follows: (1) lack of paravalvular leakage around the replacement valve, which can be advantageously examined while blood is flowing through the valve since these delivery systems allow for flow through and around the valve; (2) optimal rotational orientation of the replacement valve relative to the coronary arteries; (3) the presence of coronary flow with the replacement valve in place; (4) correct longitudinal alignment of the replacement valve annulus with respect to the native patient anatomy; (5) verification that the position of the sinus region of the replacement valve does not interfere with native coronary flow; (6) verification that the sealing skirt is aligned with anatomical features to minimize paravalvular leakage; (7) verification that the replacement valve does not induce arrhythmias prior to final release; and (8) verification that the replacement valve does not interfere with function of an adjacent valve, such as the mitral valve.

With particular reference to the delivery of the stent embodiments described herein, one or both of the inflow barbs 50 and outflow barbs 60 can further assist in anchoring the stent within its desired location within the patient. That is, the fact that these barbs 50, 60 extend generally into the saddle area 70 can be used to prevent migration in both the retrograde and antegrade directions by attaching both to the leaflets and to the annular region. In particular, when the stent 10 is being implanted, the delivery system can be deployed either slightly low in the anatomy, after which it is pulled back to engage the inflow barbs 50, or can be deployed slightly high in the anatomy, after which it is pushed forward to engage the outflow barbs 60. The amount of movement to engage either of these sets of barbs can be relatively minimal, yet their engagement with tissue can provide a desired additional amount of anchoring of the stent.

It is further contemplated that the devices and methods of the invention may include only one set of barbs that extend toward the saddle area of the device. For example, the stent structure may include only a set of inflow barbs or a set of outflow barbs, which would be implanted in a patient using a method that includes engagement of one set of barbs with the anatomy of the patient.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A stented valve comprising:
   a stent structure comprising a generally tubular body portion, an interior area, a longitudinal axis, a proximal end, a distal end, an outer surface comprising a concave saddle area between the proximal and distal ends, a first row of a first plurality of adjacent V-shaped structures distal of the concave saddle area that extend from each other around a first circumference of the stent structure, and a second row of a second plurality of adjacent V-shaped structures proximal of the concave saddle area that extend from each other around a second circumference of the stent structure, wherein the first row of the plurality of adjacent V-shaped structures is proximal of the distal end of the stent structure;
   a first barb extending proximally from the first row of V-shaped structures, wherein the first barb extends over at least a portion of the concave saddle area of the stent structure;
   a second barb extending distally from the second row of the plurality of V-shaped structures, wherein the second barb extends from a location distal of the proximal end of the stent structure; and
   a valve structure attached within the interior area of the stent structure, the valve structure comprising a plurality of leaflets.

2. The stented valve of claim 1, wherein the first barb extends outward from the outer surface of the stent structure.

3. The stented valve of claim 1, further comprising a first row of diamond-shaped structures, wherein the first row of V-shaped structures forms a portion of the first row of diamond-shaped structures.

4. The stented valve of claim 3, wherein the first row of diamond-shaped structures comprises a first plurality of stent crowns disposed at a distal end of the stent structure.

5. The stented valve of claim 1, wherein the first barb comprises a distal end that is spaced from the outer surface of the stent structure.

6. The stented valve of claim 1, wherein the first barb comprises a tip that is sharp enough to penetrate tissue.

7. The stented valve of claim 1, wherein the first barb comprises a first plurality of barbs extending proximally from the first row of the plurality of V-shaped structures and spaced from each other around the periphery of the outer surface of the stent structure.

8. The stented valve of claim 1, wherein a diameter of the first circumference and a diameter of the second circumference are both greater than a diameter of the concave saddle area.

9. The stented valve of claim 1, wherein the first barb extends at an angle away from the longitudinal axis of the stent structure.

10. The stented valve of claim 1, wherein the first barb extends from a junction of wire segments of the first row of the plurality of V-shaped structures.

11. The stented valve of claim 10, wherein the junction is at a proximal end of the first row of the plurality of V-shaped structures.

12. The stented valve of claim 1, wherein the second barb extends from a distal end of the second row of the plurality of V-shaped structures.

13. The stented valve of claim 1, wherein the second barb extends from a junction of wire segments of the second plurality of V-shaped structures.

14. The stented valve of claim 1, wherein the second row of the plurality of V-shaped structures is disposed at a proximal end of the stent structure.

15. The stented valve of claim 1, wherein the second barb comprises a second plurality of barbs extending distally from the second row of the plurality of V-shaped structures and spaced from each other around the periphery of the outer surface of the stent structure.

16. A stented valve comprising:
   a stent structure comprising a generally tubular body portion, an interior area, a longitudinal axis, an inflow end, an outflow end, an outer surface comprising a concave saddle area between the inflow and outflow ends, a first row of a first plurality of adjacent V-shaped structures disposed towards the outflow end relative to the concave saddle area that extend from each other around a first circumference of the stent structure, and a second row of a second plurality of adjacent V-shaped structures disposed towards the inflow end relative to the concave saddle area that extend from each other around a second circumference of the stent structure, wherein the first row of the plurality of adjacent V-shaped structures is disposed spaced from the outflow end of the stent structure;
   a first plurality of barbs extending towards the inflow end from the first row of V-shaped structures;
   a second plurality of barbs extending towards the outflow end from the second row of V-shaped structures, wherein the second plurality of barbs extend from an outflow end of the second row of V-shaped structures;
   wherein at least one the first plurality of barbs or the second plurality of barbs extends over at least a portion of the concave saddle area of the stent structure; and
   a valve structure attached within the interior area of the stent structure, the valve structure comprising a plurality of leaflets.

17. The stented valve of claim 16, wherein the first plurality of barbs extend from an inflow end of the first row of V-shaped structures.

18. The stented valve of claim 16, wherein the second row of V-shaped structures is disposed at the inflow end of the stent structure.

* * * * *